United States Patent
Gordon (12)

(10) Patent No.: US 6,280,191 B1
(45) Date of Patent: Aug. 28, 2001

(54) DISTRACTOR SUITABLE FOR PERMANENT IMPLANTATION INTO BONE

(76) Inventor: Christopher B. Gordon, 617 S. Pitt St., Alexandria, VA (US) 22314

( * ) Notice: Subject to any disclaimer, the term of this patent is extended or adjusted under 35 U.S.C. 154(b) by 0 days.

(21) Appl. No.: 09/389,246

(22) Filed: Sep. 3, 1999

(51) Int. Cl.[7] ........................................ A61C 8/00
(52) U.S. Cl. ................ 433/173; 606/90; 623/16
(58) Field of Search .................. 606/90, 72, 73, 606/63–65, 53, 104; 623/16, 11; 433/172–176

(56) References Cited

U.S. PATENT DOCUMENTS

| | | |
|---|---|---|
| 5,108,394 | 4/1992 | Kurokawa et al. . |
| 5,139,424 | 8/1992 | Yli-Urpo . |
| 5,527,183 | 6/1996 | O'Brien . |
| 5,540,687 | 7/1996 | Fairley et al. . |
| 5,584,695 * | 12/1996 | Lal Sachdeva et al. ............. 433/173 |
| 5,700,263 | 12/1997 | Schendel . |
| 5,704,939 | 1/1998 | Justin . |
| 5,807,382 | 9/1998 | Chin . |
| 5,810,812 | 9/1998 | Chin . |
| 5,839,899 | 11/1998 | Robinson . |
| 5,846,245 | 12/1998 | McCarthy et al. . |
| 5,899,696 * | 5/1999 | Shimoda ............................... 433/173 |
| 5,899,940 * | 5/1999 | Carchidi et al. ....................... 623/16 |
| 5,961,329 * | 10/1999 | Stucki-McCormick .............. 433/173 |
| 5,976,142 * | 11/1999 | Chin ....................................... 606/73 |
| 6,050,819 * | 4/2000 | Robinson ............................. 433/173 |
| 6,126,662 * | 10/2000 | Carmichael et al. .................. 606/72 |

OTHER PUBLICATIONS

Fang, Jianming; Zhu, Yao–Yao; Smiley, Elizabeth; Bonadio, Jeffrey; Rouleau, Jeffrey; Goldstein, Steven A.; McCauley, Laurie K.; Davidson, Beverly L.; and Roessler, Blake J.; "Stimulation of new bone formation by direct transfer of osteogenic plasmid genes".

Lind, M.; "Growth factor stimulation of bone healing. Effects on osteoblasts, osteomies, and implants fixation."; Acta Orthop Scand Suppl 1998 Oct.; 283:2–37.

Radomsky, M.L.; Thompson, A.Y.; Spiro, R.C.; Poser, J.W.; "Potential role of fibroblast growth factor in enhancement of fracture healing."; Clin Orthop Oct. 1998; (355 Suppl):S283–93.

Welch, R.D.; Jones, A.L.; Bucholz, R.W.; Reinert, C.M.; Tjia, J.s.; Pierce, W.A.; Wozney, J.M.; Li, X.J.; "effect of recombinant human bone morphogenetic protein–2 on fracture healing in a goat tibial fracture model."; J. Bone Miner Res Sep. 1998; 13(9):148.

Bostrom, M.P.; Camacho, N.P.; "Potential role of bone morphogenetic proteins in fracture healing."; Clin Orthop Oct. 1998; (355 Suppl):S274–82.

Rosier, R.N.; O'Keefe, R.J.; Hicks; "The potential role of transforming growth factor beta in fracture healing."; Clin Orthop Oct. 1998; (355 Suppl):S294–300.

Cook, S.D.; Salkeld, S.L.; Rueger, D.C.; "Evaluation of recombinant human osteogenic protein–1 (rhOP–1) placed with dental implants in fresh extraction sites."; J Oral Imploantol 1995; 21(4):281–9.

(List continued on next page.)

Primary Examiner—David O. Reip
Assistant Examiner—(Jackie) Tan-Uyen T. Ho
(74) Attorney, Agent, or Firm—Arter & Hadden LLP

(57) ABSTRACT

The present invention relates to an osteogenic distractor suitable for indexed osteotomy following permanent implantation into bone. The osteogenic distractor may be a means for anchoring two or more sections of bone and a means for facilitating movement of one section of anchored bone relative to another section of anchored bone. Furthermore, the continuous tension on the bone produced by the distractor may facilitate stimulation of osteogenesis around the implant.

23 Claims, 10 Drawing Sheets

OTHER PUBLICATIONS

Lee, M.B.; "Bone morphogenetic proteins: background and implications for oral reconstruction. A review."; J Clin Periodontol Jun. 1997; 24(6):355–65.

Trippel, S.B.; "Potential role of insulinlike growth factors in fracture healing."; Clin Orthop 1998; (355 Suppl):S301–13.

Rutherford, R.B.; Sampath, T.K.; Rueger, D.C.; Taylor, T.D.; "Use of bovine osteogenic protein to promote rapid osseointegration of endosseous dental implants."; Int J Oral Maxillofac Implants 1992 Fall; 7(3):297–301.

Bonn, Dorothy; "The appication of cell biology to broken bones"; The Lancet, Feb. 20, 1999; vol. 353, No. 9153, p. 650.

Nemcovsky, C.E.; "Alveolar Ridge Preservation Following Extraction of Maxillary Anterior Teeth. Report on 23 Consecutive Cases"; J. Periodontol. 1966; 67(4):390–395.

Ace Dental Implant System; "Innovative Technology for the New Millenium . . . with the ACE OsteoGenic Distractor".

* cited by examiner

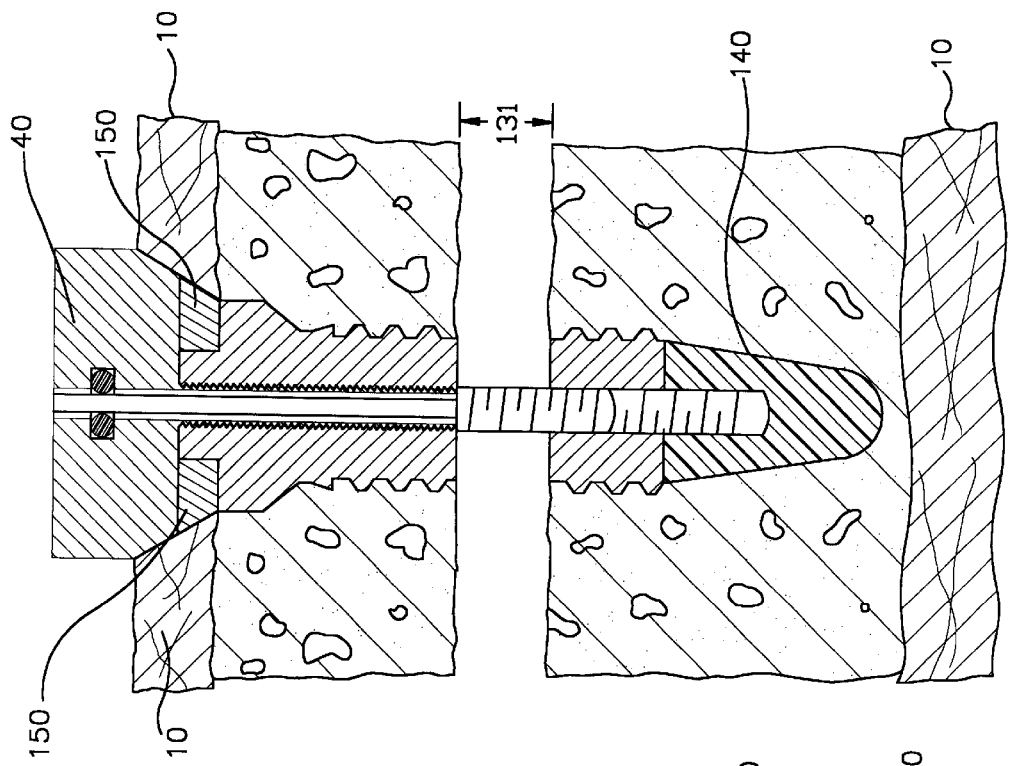
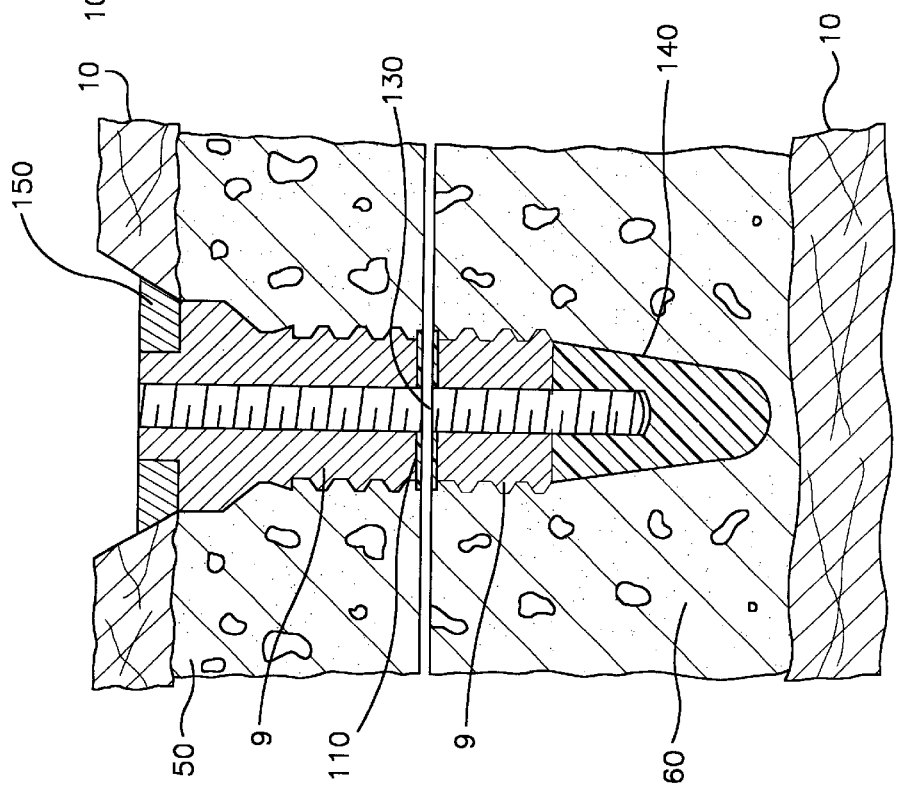

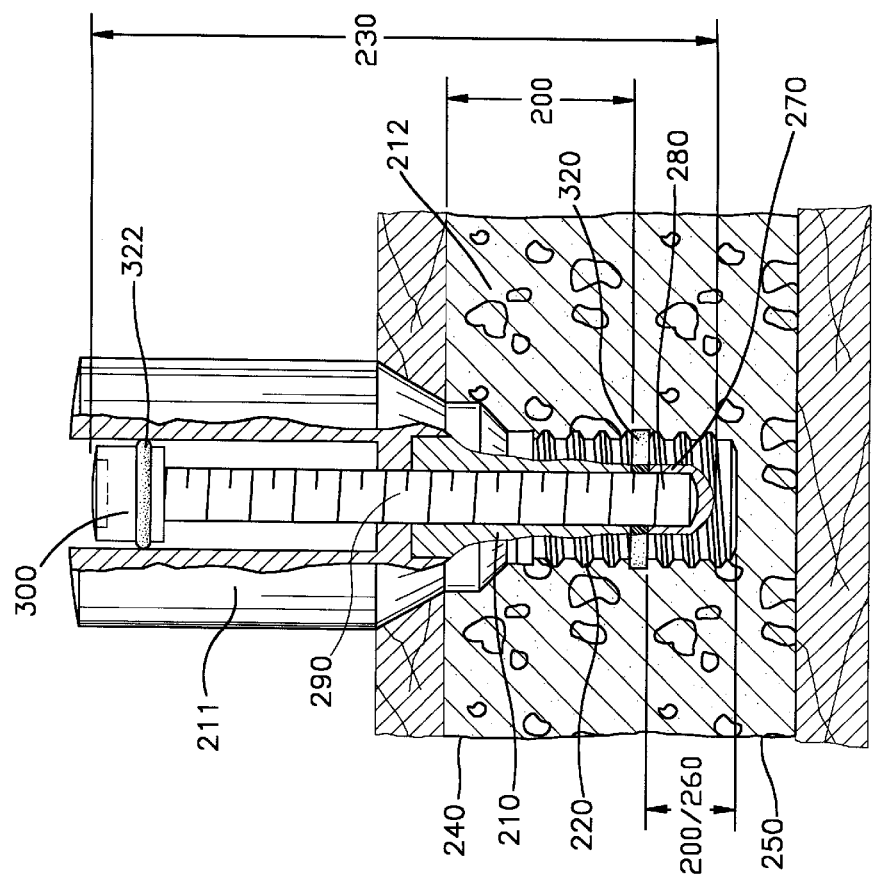
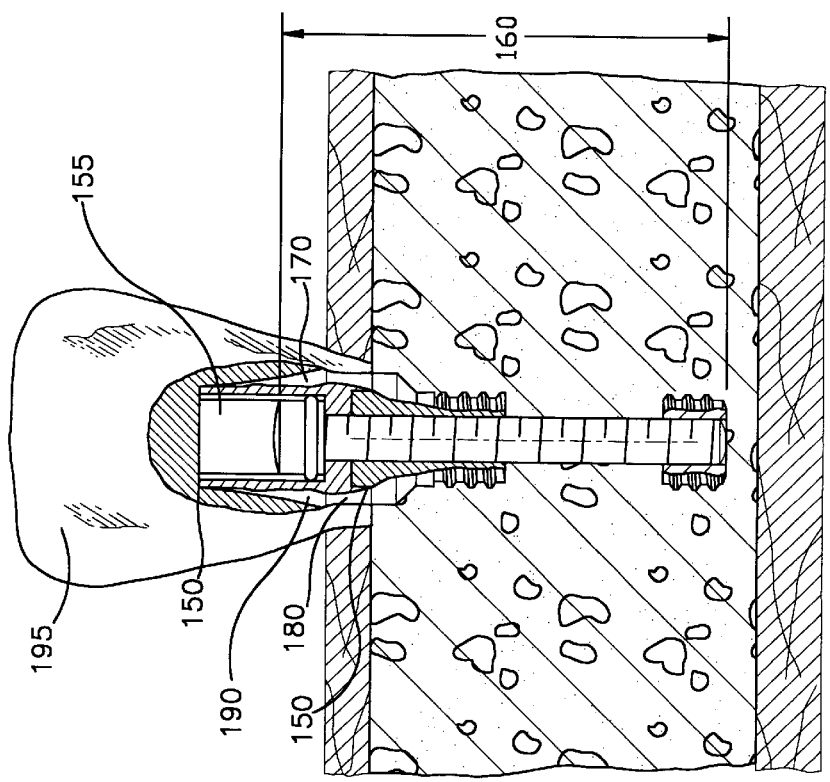
Fig.4A
Fig.3D

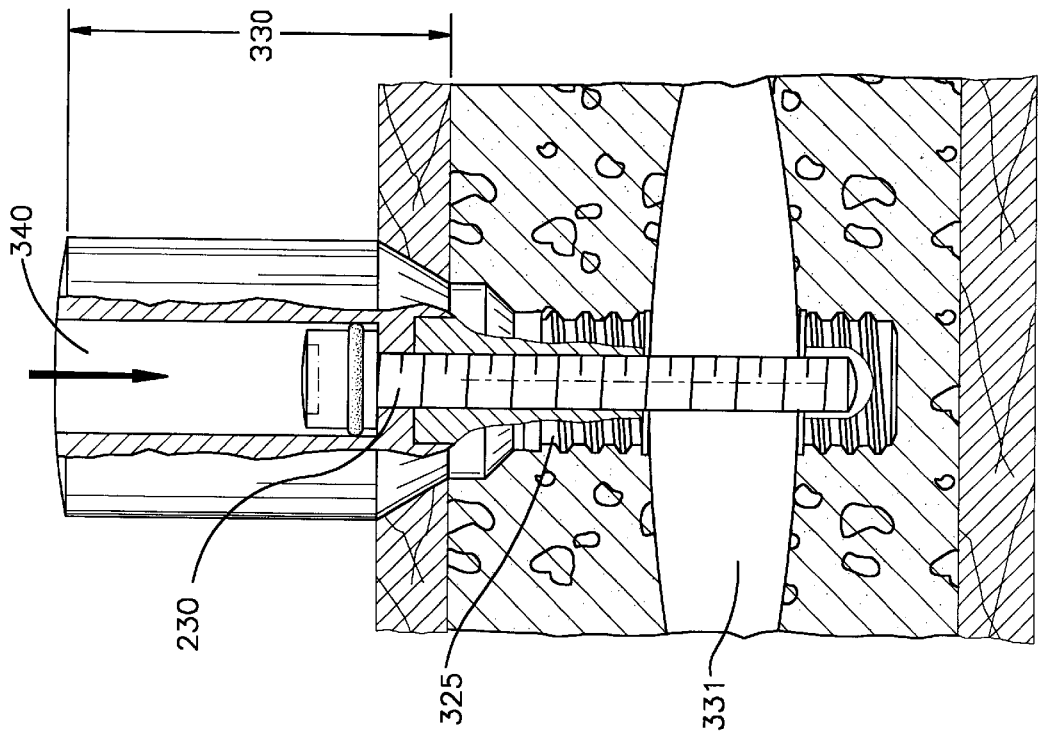
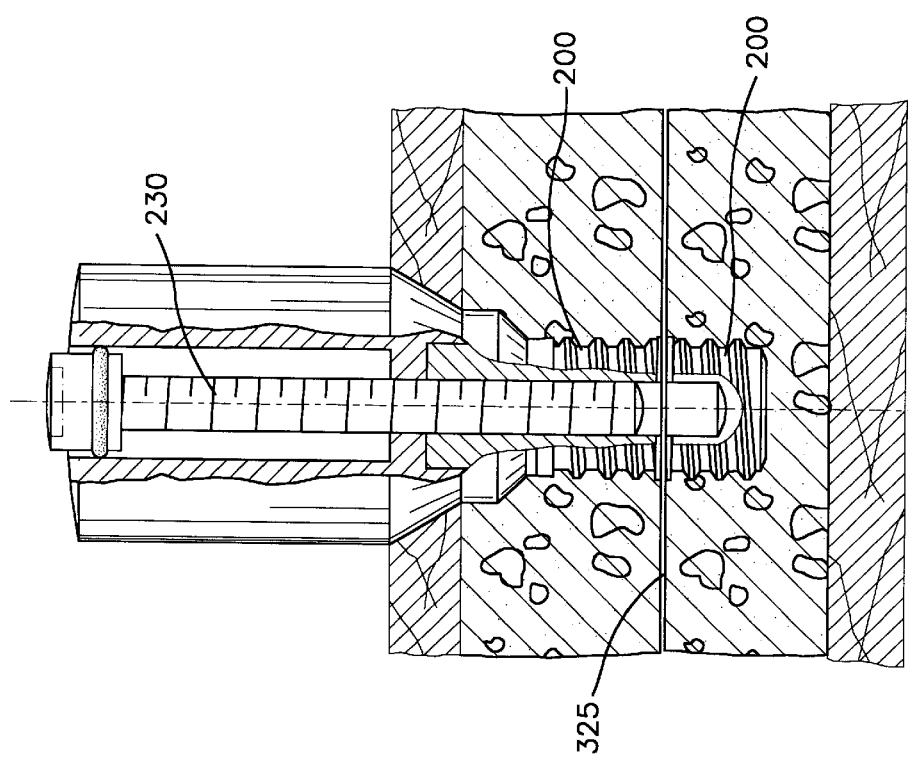
Fig.4C
Fig.4B

DISTRACTOR SUITABLE FOR PERMANENT IMPLANTATION INTO BONE

FIELD OF THE INVENTION

The present invention relates generally to devices and methods for the distraction of bone. More specifically, the invention includes distraction osteogenesis involving a distractor suitable for permanent implantation into bone, preferably alveolar bone.

BACKGROUND OF THE INVENTION

Orthopedic surgeons have relied upon the process of distraction osteogenesis to reconstruct and lengthen bones. This process may involve placing a vascularized piece of bone under tension, thereby inducing native bone formation via the creation of a bony reparative callus, which can then placed under tension to generate new bone. To effect distraction osteogenesis, a surgeon generally performs an osteotomy, thereby sectioning or segmenting the bone to be altered into more than one piece. As the bone heals, it can slowly and gradually expand over a period of time so that the blood vessels and nerve ends remain intact during the distraction process. For example, the bone may be extended a millimeter a day, often by performing two extensions of half a millimeter, for three or four weeks.

As the gap between the bone segments widens, the natural healing capacity of the body can fill the void with new bone and adjacent soft tissue. Once the desired bone formation is achieved, the area may be allowed to heal and consolidate. Often, the distraction osteogenesis device is then removed.

Known distraction osteogenesis devices may present numerous disadvantages. First, distraction osteogenesis devices are generally external, which may cause a number of problems or complications. Often, cumbersome metal rods and rings located external to an individual's skin are used to distract or separate bone segments. Individuals, and in particular small children, may fall and injure themselves on the protruding metal edges. Further, small children may complicate the distraction osteogenesis procedure by improperly adjusting the osteogenesis distraction device. The distraction osteogenesis device may require multiple entry points to an individual's skin and thus may create multiple scars. Distraction osteogenesis devices requiring multiple entry points may also increase the likelihood of infection due to the multiple openings in the individual's skin. Also, individuals undergoing the distraction osteogenesis procedure have to cope with an external device, which is not cosmetically appealing.

A second problem encountered with distraction osteogenesis devices regards customizing devices for individuals. Generally, a distraction osteogenesis device used for one individual would not be suitable for another. In distraction osteogenesis devices used in the craniofacial area, for example, distraction osteogenesis devices must be measured to fit specific surface areas of craniofacial bones. Also, individuals may have different amounts of bone caused by different types of birth abnormalities or accidents, thus requiring customized distraction osteogenesis devices due to limited bone.

Third, distraction osteogenesis devices are attached to bone segments in such a way that the point of fixation to the bone transfers force during activation. For example, a distraction osteogenesis device may be attached to a bone segment by a bone screw or rod, which transfers a substantial amount of force during activation or when the distraction osteogenesis device is exerting pressure between the bone segments. By having the bone screw transfer a substantial amount of the force during activation, the distraction osteogenesis device may be dislodged from the bone.

Fourth, distraction osteogenesis devices are activated using constant rates, which do not reflect the individual's healing abilities. Regardless of the age or condition of the individual, distraction osteogenesis devices are typically activated by widening the gap between bone segments 0.125 mm to 0.50 mm four times per day. This conventional activation rate results in bone growth as low as 20 mm in 20 days. Accordingly, an individual may have to be under constant medical supervision for up to 20 days. An individual could be an outpatient, but would need to return to the hospital four times per day for adjustments. Present distraction osteogenesis device activation techniques do not take into account an individual's ability to grow bone at a greater or lesser rate. By using this constant rate, bone may grow too quickly and lock the distraction osteogenesis device, or in the alternative, bone may grow too slowly, requiring a longer period of time that the distraction osteogenesis device is necessary.

Therefore, it is desirable to provide a distraction osteogenesis device suitable for indexed osteotomy following permanent implantation beneath an individual's skin or soft tissue. The permanently implanted distraction osteogenesis device then could be permanently positioned within an individual, thereby eliminating the need for surgery in removing the device, including the associated risks and costs. The distraction osteogenesis device then would be more cosmetically appealing and reduce the likelihood of infection, injury and/or scarring. Further, it is desirable to have a distraction osteogenesis device that does not have to be customized for each individual. Manufacturing and medical costs would then be substantially reduced by using a standard distraction osteogenesis device and method, rather than customizing distraction osteogenesis devices and methods for each individual. The distraction osteogenesis device also should be affixed to bone in such a way that a substantial amount of the force used in activation is not transferred through a fastening device (i.e., screw, pin or rod). Finally, the distraction osteogenesis device should be activated at an optimal rate for an individual's bone growth.

To further improve the distraction osteogenesis procedure, it would desirable to enhance bone healing and bone remodeling so that the segmented bone can be expanded more rapidly over time and at the same time add increased strength and stability to the newly formed bone.

The foregoing shows a need for devices and methods for distraction osteogenesis involving a distractor suitable for indexed osteotomy following permanent implantation into bone, preferably alveolar bone.

SUMMARY OF THE INVENTION

An objective of the present invention is therefore osteogenic distraction involving a distractor suitable for indexed osteotomy following permanent implantation into bone, preferably alveolar bone (See FIG. 1).

In accomplishing these and other objectives, the present invention provides an osteogenic distractor suitable for indexed osteotomy following permanent implantation into bone, wherein the distractor comprises a means for anchoring two or more sections of bone and a means for facilitating movement of one section of anchored bone relative to another section of anchored bone.

In another embodiment of the present invention, all or part of the distractor is made of bioabsorbable material. The present invention also includes a distractor where the bioabsorbable material is selected from one or more of the group consisting of poly-D, L-lactic acid, polyethylene glycol, polydioxanone, polylactic acid, 70L/30DL polylactide, polyglycolide, poly(orthoester), calcium sodium metaphosphate, hydroxyapatite, calcium phosphate, polytetra fluoroethylene, collagen I, II, IX, X, and XI, durapatite, and hydrogel.

In yet another embodiment, the present invention includes a distractor that comprises a means for excluding the external environment. In a preferred embodiment, the present invention involves implantation of the distractor into alveolar bone. One other embodiment of the present invention includes a distractor capable of engaging a dental prosthesis (See FIG. 2).

In addition, the present invention may comprise a chemical or biological composition capable of stimulating or enhancing the attachment an/or rentention of the distractor anchoring means to the bone following implantation.

The present invention also preferably provides methods for osteogenic distraction comprising implanting of a distractor into bone, performing an indexed osteotomy, and operating the means for facilitating movement of one section of anchored bone relative to another section of anchored bone. In another embodiment, the present invention fiurther comprises engaging the distractor with a dental prosthesis.

Other objectives, features, and advantages of the present invention will become apparent from the following detailed description. The detailed description and the specific examples, while indicating preferred embodiments of the invention, are provided by way of illustration only. Accordingly, the present invention also includes those various changes and modifications within the spirit and scope of the invention that may become apparent to those skilled in the art from this detailed description.

BRIEF DESCRIPTION OF THE FIGURES

FIG. 3B is a schematic of an embodiment of the present invention in a submerged profile, where the screw 40 has been removed, and following the indexed osteotomy 130, is ready to receive the screw and abutment.

FIG. 3C shows an embodiment of the present invention in a submerged profile at maximum distraction 131, ready for change to the restoration abutment and a permanent screw.

FIG. 3D depicts an embodiment of the present invention in a submerged profile after distraction, with a permanent screw 160, restoration abutment 150, and dental crown 195 in place.

FIG. 4A provides a cross-sectional perspective of an embodiment of the present invention showing the extended profile distractor. The two halves of the osteogenic distractor separated by an absorbable disk 320, embedded in the alveolar bone 212. The distraction abutment 211 is in place and the distractor screw 230 is at the beginning of its travel. The surgeon can back out the screw to permit a saw blade to pass through the absorbable disk 320, making the osteotomy at the correct indexed level.

FIG. 4B shows the extended profile device after the screw 230 has been backed out and the bony osteotomy 325 made between the two halves of the distractor 200.

FIG. 4C depicts the extended profile device and the newly produced bone 331 after the complete distraction.

DETAILED DESCRIPTION OF THE PREFERRED EMBODIMENTS

Figure 1:
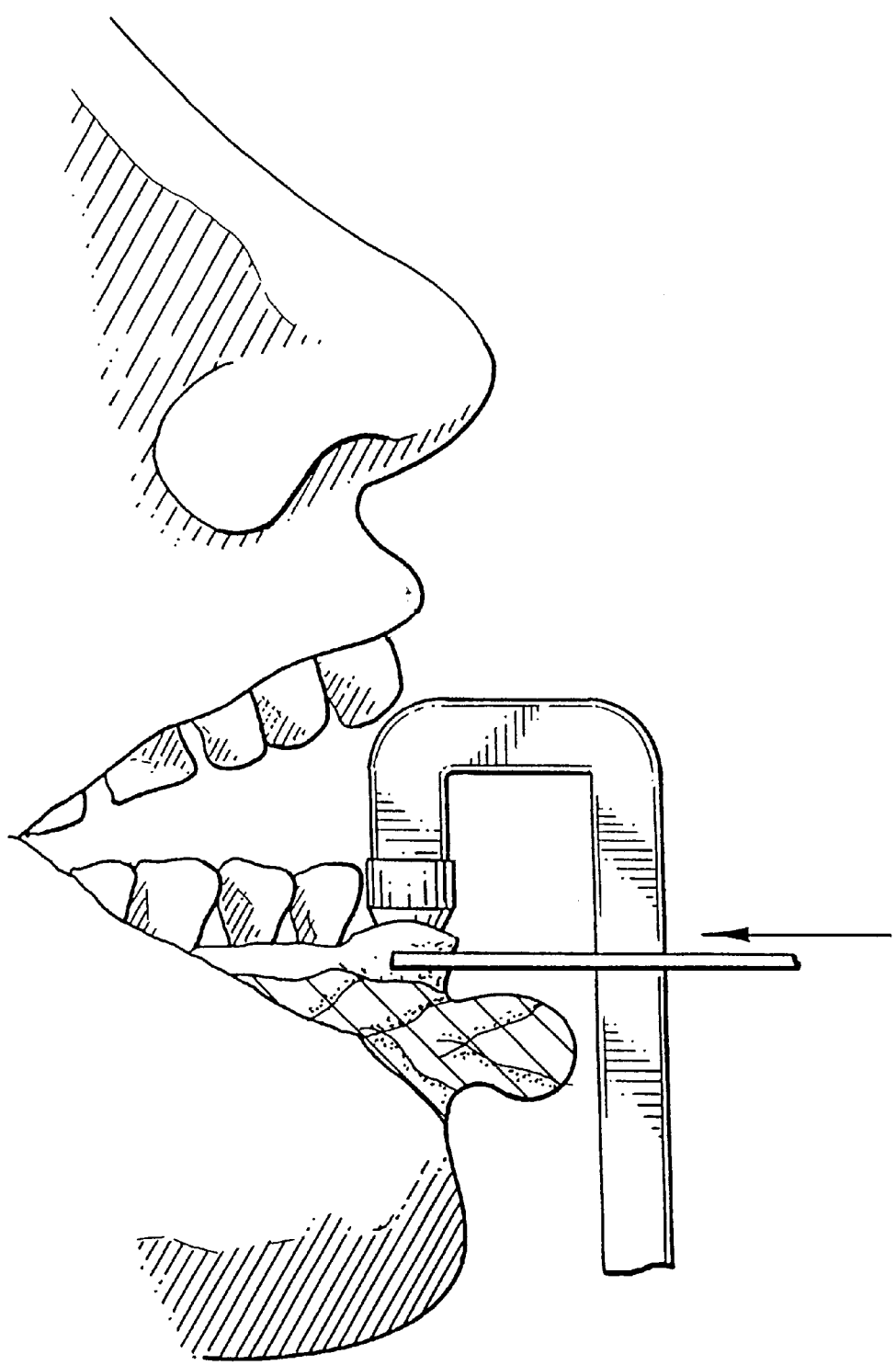
FIG. 1 is a schematic of the osteotomy jig, permitting the surgeon to make the bony cut at the correct indexed location with an embodiment of the present invention implanted appropriately in the alveolar bone.
Figure 2:
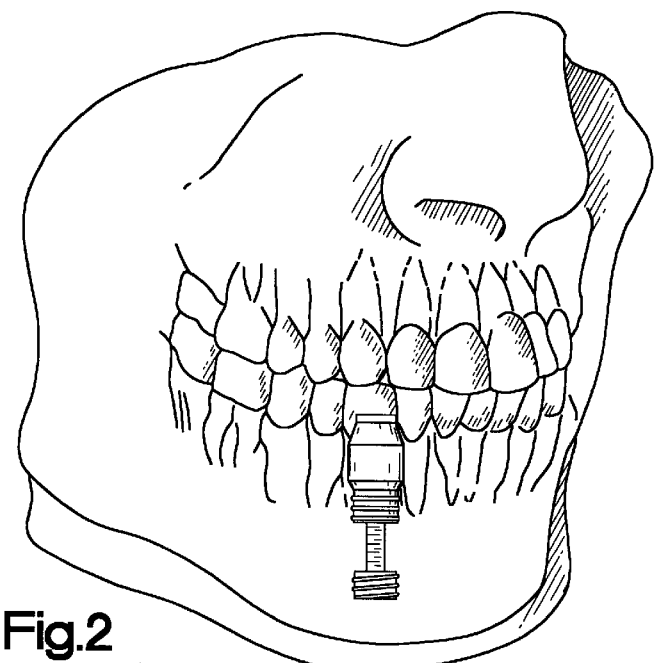
FIG. 2 depicts an embodiment of the present invention after complete distraction, with the restoration abutment and the dental crown in place.

The present invention may include various embodiments of an osteogenic distractor suitable for indexed osteotomy following permanent implantation into bone, where the distractor comprises a means for anchoring two or more sections of bone and a means for facilitating movement of one section of anchored bone relative to another section of anchored bone. As such, the distractor, including the anchoring means and the movement means, may be made of any biocompatible material, and preferably, bioabsorbable material. Movement may refer to any change in position along various geometric axes (X, Y and Z) in isolation or in concert.

In addition, embodiments of the present invention may include a single piece or multiple section distractor anchoring means. Whether the distractor anchoring means comprises a single piece or multiple sections, the anchoring means may preferably be made of material suitable for separation into sections through indexed osteotomy following permanent implantation of the distractor into bone. This may further include pre-scored sites along the anchor means or discrete sections comprising materials with relatively different tolerances for separation by osteotomy. In additional prefered embodiments, the distractor anchoring means further comprises a chemical or biological composition capable of activating, stimulating, or enhancing the attachment and/or retention of the distractor anchoring means to the bone following implantation.

Certain embodiment of the present invention may also include movement means capable of facilitating movement of one section of anchored bone relative to another section of anchored bone, along various geometric axes, in isolation or in concert. One example may be a threaded cylinder or screw used to engage the various sections of the distractor anchoring means to facilitate movement following the indexed osteotomy. Other examples could include an air or liquid chamber, pneumatic cylinder, or high tensile fiber or cable. However, any means known in the art for facilitating movement of one section of a sectional housing relative to another section could be used. Preferably, the movement means would comprise elements to facilitate the controlled movement of one section of anchored bone relative to another section of anchored bone. Such elements could include pre-defined stop or rachet points along the movement means or anchoring means, or comprise an automated engine and controller mechanism.

One way to enhance bony healing during this surgical procedure would be to introduce bone growth factors such as bone morphogenetic proteins (BMPs) and basic fibroblast growth factor (bFGF) to the area of distraction. These two classes of bone growth factors have been shown to accelerate bone regeneration, bone healing to prosthetic-like implants, and increase strength and stability to the bony callus. The bone growth factors could be delivered to the area of distraction by a variety of methods. One method would be to introduce the bone growth factors in combination with a collagen matrix, which could be a gel- or sponge-like material, to the area of distraction. The bone growth factor would stimulate the patient's own bone cells into action, while the collagen would provide the scaffolding into which the stimulated bone cells can grow. In the end, bone could replace the collagen scaffold, which may be eventually resorbed.

Another method of delivery could be to coat the actual distraction device with the bone growth factor in combination with hydroxyapatite, which would have a synergic stimulative effect on the bone cells. For this to be accomplished, a specific amount of the bone growth factor would be absorbed to a gritblasted hydroxyapatite coated implant or distraction device prior to implantation.

However, an alternate method to the delivery of recombinant bone growth factors, would be gene therapy. Delivery by gene therapy may be more cost effective because ex vivo production of DNA for clinical use is inexpensive compared with traditional methods of protein production. Also, gene therapy may be a more efficient way to deliver the bone growth factors compared with traditional protein delivery. One desirable way to utilize gene therapy in the distraction osteogenesis procedure would be to introduce plasmid-encoded proteins capable of inducing bone growth to the area of distraction. This could be accomplished by introducing biodegradable matrices, such as collagen sponges, containing expression plasmid DNA encoding bone growth factors, also known as gene-activated matrices (GAMs), to the area of distraction.

The embodiment of the present may be applicable to a number of surgical applications, which include, but is not limited to, mandibular distraction, genial angle distraction, mental distraction, cranial vault distraction, midface distraction, and mentoplasty.

Without further elaboration, one skilled in the art with the preceding description can utilize the present invention to its fullest extent. The following examples are illustrative only, and not intended to limit the remainder of the disclosure in any way.

EXAMPLE ONE

The Submerged Profile Device

Figure 3A:
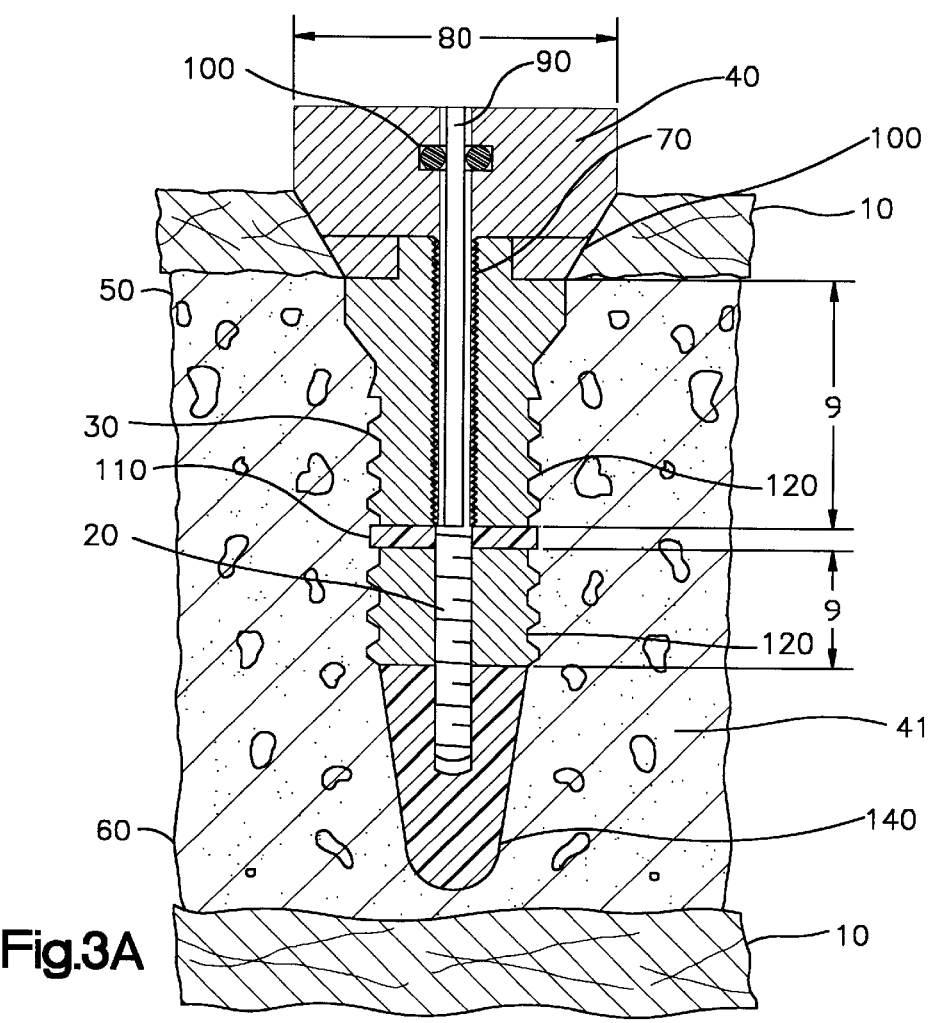
FIG. 3A depicts a cross-sectional perspective of an embodiment of the present invention in submerged profile, showing the two halves of the distractor 120 separated by the absorbable disk 1110, embedded in alveolar bone 41. The surgeon can back out the distraction screw 40, permitting a saw blade to pass through the absorbable disk 110, making the osteotomy at the correct level.

Alveolar distractors: One specific example of the present invention may involve a submerged profile device as shown in FIGS. 3A–3D, which may be constructed from titanium, stainless steel, or other hardened material. The device may be implantable or may be inserted under an individual's or animal's soft tissue and/or skin layer 10. The submerged profile device, as shown in FIG. 3A, may include two hollow 9, internally 20 and externally 30 threaded cylinders that may be used to carry the load of the distractor screw 40, applying vertical forces to the superior 50 and inferior 60 segments of the alveolar bone 41. This specific device may comprise a distractor screw 40, and has threads 70 pitched such that there is approximately of travel for a 180° turn of the screw 40. The screw 40 may have a cylindrical head 80 with an internal hex drive design 90, and can have a groove for an O-ring 100 to isolate the device from the oral environment. Also, it may have an absorbable shim disk 110 constructed from a bioabsorbable material and used to join the two halves of the distractor 120 for implantation. The absorbable shim disk 110 may be subsequently cut through for the indexed osteotomy 130 as shown in FIG. 3B. This design can allow the two halves 9 to be inserted as a unit, and to then allow an indexed bony osteotomy 130 to be performed blindly between the two halves of the device (See FIG. 3B). In addition, there may be an absorbable cap 140 to protect soft tissues 10 from the screw 40 during the distraction 131 period, which also may serve to isolate the device from the sinus environment if used in a maxillary location (See FIG. 3C). Furthermore, the device, as shown in FIG. 3D, can contain an abutment shim 150, which is a conical disk with a hexagonal central gap 155 to fit between the implant 160 and the threaded healing abutment 170. This healing abutment 170 may have both external threads 180 to engage the implant 160 and a smooth-walled screw channel 190 to retain the distraction screw in the internal space. It may also provide a conformer for the healing gum, and the final restoration post to accept the dental restoration 195.

FIGS. 3A, 3B, 3C, and 3D are a sequential representation of the present invention showing the distraction process using the submerged profile device for the endetulous patient. FIG. 3A reveals the submerged profile device with the distraction screw passing through the distal portion of the distractor, and its protective sleeve to isolate the screw from the soft tissue or the sinus, depending on the placement of the device. The distraction screw is backed out of the submerged profile device allowing the surgeon to pass a saw blade through the absorbable disk, making the osteotomy at the correct level (See FIG. 3B). Following osteotomy, the distraction screw can be replaced and may be activated until the desired height of distraction is reached (See FIG. 3C). After maximum distraction has been reached, the distraction screw may be changed for a permanent screw and the restoration abutment may be attached along with the dental crown (See FIG. 3D).

Figure 4D:
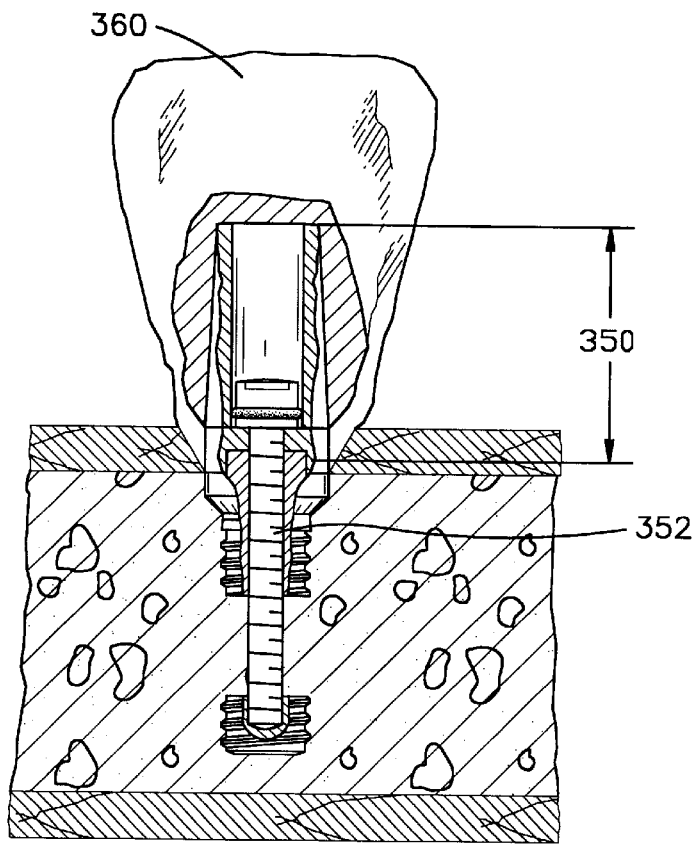
FIG. 4D shows the extended profile device where the healing/distraction abutment has been removed, and the restoration abutment 350 and the final screw 352 have been placed, with the denial crown 360 cemented upon the abutment 350, which may comprise the final form of the implant restoration.

The Extended Profile Device: The present invention may involve an extended profile device (See FIGS. 4A–4D) as shown in FIG. 4A, the extended profile device can have two hollow, internally 210 and externally 220 threaded cylinders 200. The cylinders may be used to carry the load of the distractor screw 230 by applying vertical forces to the superior 240 and inferior 250 segments of the alveolar bone 212. These cylinders 200 can form the distractor/implant proper. The distal portion can have a blind end 260 threaded internally proximally 270. The distractor screw 230 has a blunt tip 280, which spins within the distal end 260, applying the distraction force to the distal distractor 260. The screw 230 may have threads 290 with a pitch, which is calibrated to achieve 0.25 mm–1.0 mm of expansion daily, corresponding to either full or half turns to make control easier for the patients. The head of the distractor screw 300 may be cylindrical, may have an internal hex drive design 310, and a groove for an O-ring 320, which may be used to isolate the device from the oral environment. In addition, the distractor screw 230 may have a blunt, threadless tip 280, which spins inside of the distal distractor 260. The extended profile device may also have a shim disk 320, which can be used to join the two halves of the distractor for implantation. This design permits the two halves 200 of the distractor to be inserted as a unit and subsequently allow an indexed bony osteotomy 325 to be performed blindly between the two halves of the device 200 (See FIG. 4B). Furthermore, the embodiment can have an extended profile-healing abutment 330 (See FIGS. 4B and 4C). In a preferred embodiment, the healing abutment may have a hex recess 340 in its base to mate with the implant and internal screws for the distraction screw 230. The distraction screw 230 may engage both the abutment 330 and the proximal distractor 325 to hold the abutment in place while the distraction is underway and provide a conformer for the healing gum (See FIG. 4C). After the healing process, the healing abutment is replaced for the permanent abutment post 350, which accepts the dental restoration 360 (See FIG. 4D).

For alveolar ridge augmentation, previous technology has focused on osteoinduction using membranes, or has utilized standard bone graft techniques. Early attempts at alveolar ridge augmentation using bony distraction have incorporated external devices, which are fixed in trans-osseous screws and must be removed in order to proceed to the implantation phase of dental restoration.

This extended profile device is unique in that it utilizes the two threaded cylinders as the proximal and distal ends of an adjustable implant and uses the setscrew as a distraction mechanism to distract the basal and alveolar bone until the limits of the screw are reached. This process creates new bone between the two threaded cylinders and at the same time permits tailoring of the alveolus to achieve the desired new conformation to attain both the restorative goals and the need for bony augmentation. After a period of consolidation, the screw is then changed for the permanent screw, which retains the restoration post. The prosthodontist then applies the permanent crown, completing the restoration. This device eliminates the intervening step of implant placement and permits the period of distraction to serve as a period of consolidation as well. In addition, the fact that the implant comprises the two larger diameter cylinders and a narrower distraction screw theoretically gives the construct greater purchase in the bone and is less prone to loosening.

EXAMPLE TWO

Absorbable Distractors

Figure 5A:
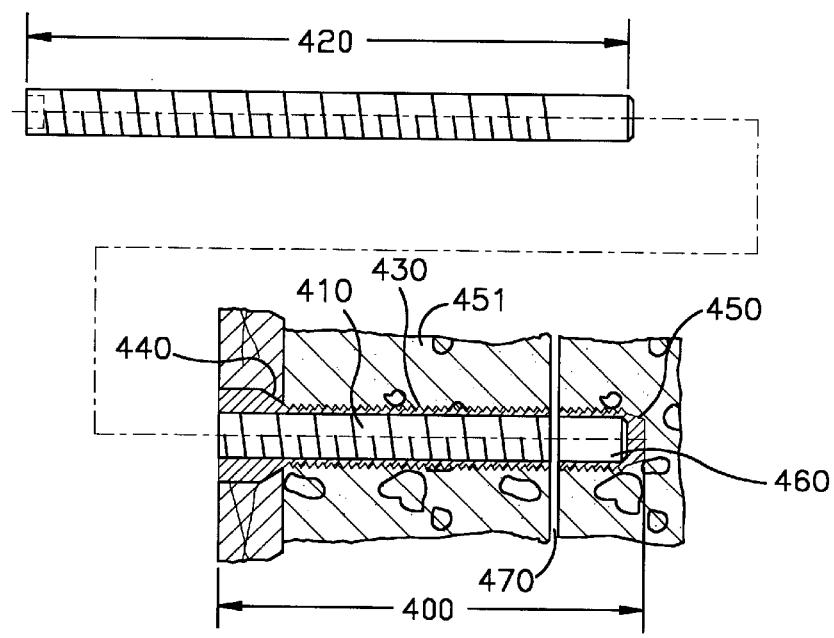
FIG. 5A provides a cross-sectional view of the present invention showing the Malar/Mandibular distractor. The distractor 400 is embedded in alveolar bone 451 and an osteotomy 470 has been performed.
Figure 5B:
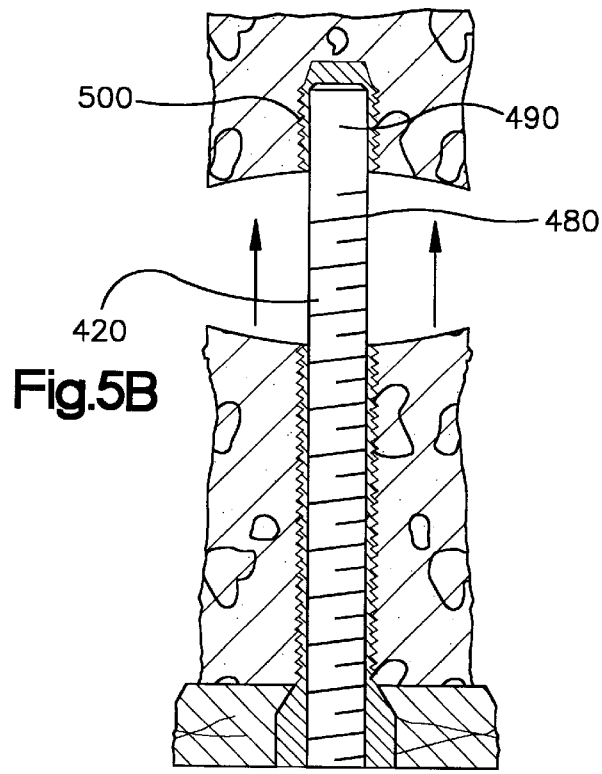
FIG. 5B depicts a cross-sectional view of the Malar/Mandibular distractor, where the distraction screw 420 has been introduced after osteotomy and maximum distraction has been achieved.
Figure 5C:
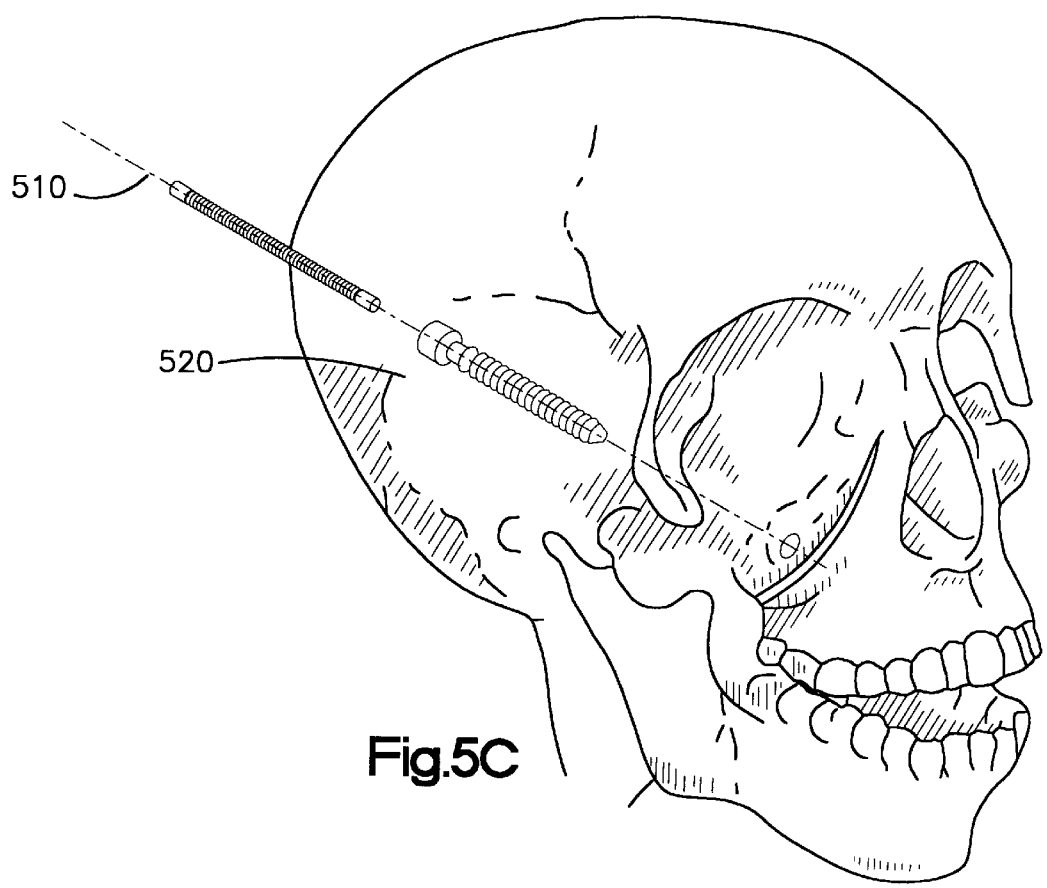
FIG. 5C depicts an application of the Malar/Mandibular distractor. The distractor is placed percutaneously under the scalp 520 and has a flexible cable tensioner 510 to permit distant activation.

Malar distractor/Mandibular distractor: The present invention may involve an absorbable malar distractor/mandibular distractor, which can have an absorbable sleeve (See FIGS. 5A–5C). The absorbable sleeve 400 may be constructed out of, but not limited to, polylactic acid, bone allograft, and hydroxyapatite coral. In a preferred embodiment, the absorbable sleeve may be constructed out of polylactic acid, threaded both internally 410 to accept the distraction screw 420, and externally 430 with larger threads to engage the bone of the canal (See FIG. 5A). The malar distractor/mandibular distractor may have a shoulder 440 and a beveled tip 450 to prevent it from over-seating (See FIG. 5A). The internal threads 410 can stop near the tip 460, and the inner surface of the tip may be smooth 460, allowing the smooth-tipped distraction screw 420 to spin without engaging the tip (See FIG. 5A). The absorbable polylactic acid may be cut at any point after the end of the internal thread stops. After the cut has been made through both the apparatus and the bone 470, the distraction screw 420 may be reintroduced, and by turning the screw, the distal portion of the apparatus and the distal bone are distracted away from the proximal segment (See FIG. 5B). The distraction screw 420, which is threaded along its length 480, may have a blunt tip 490 to spin freely inside the distal distractor 500 (See FIG. 5B). The distraction screw 420 may have a cable tensioner 510 to permit distant activation (See FIG. 5C). In an additional embodiment, both the distraction screw 420 and the cable tensioner 510 may be flexible. The treacher-Collins patient who lacks a zygomatic arch is an excellent candidate for this device. The device can be placed percutaneously and activated through the flexible cable under the scalp 520 (See FIG. 5C).

This device also consists of the basic idea of two cylinders, which are gradually distracted, but since the desired goal is merely bony augmentation, the ideal distractor satisfies the goal of bony augmentation and then resorbs. It follows, then, that the device should consist of two cylinders in a similar construct, but the treaded cylinders should be made of polylactic acid polymer. This may be fashioned in such a way as to permit the surgeon to place a single threaded cylinder and subsequently perform the osteotomies across this cylinder to facilitate the device placement. In area where there is minimal access, the two cylinders maybe placed through separate tunnels. The distal device may be internally threaded to permit distraction of the basal bone proximal to distal, or may have a blind end, which distract the proximal segment away from the distal device. Typical applications for this device could include malar augmentation and mandibular lengthening.

Figure 6A:
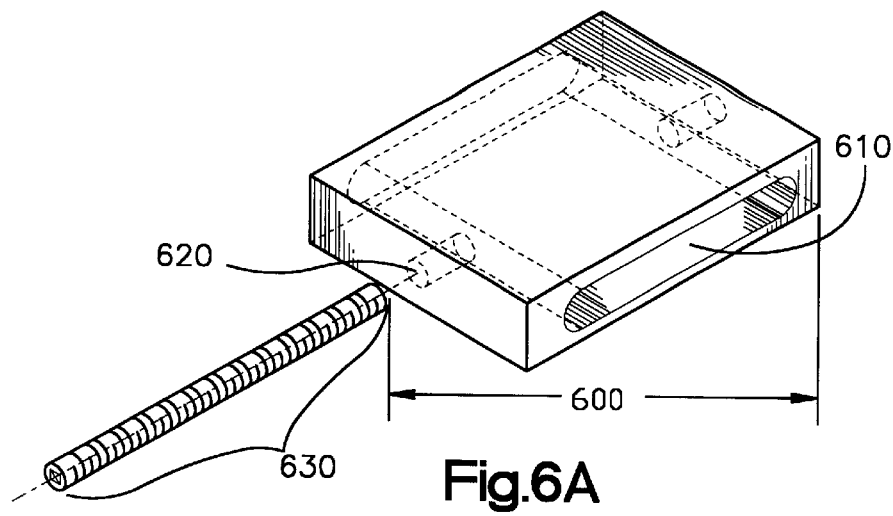
FIG. 6A is a schematic of an embodiment of the present invention, specifically showing an absorbable block distractor 600.
Figure 6B:
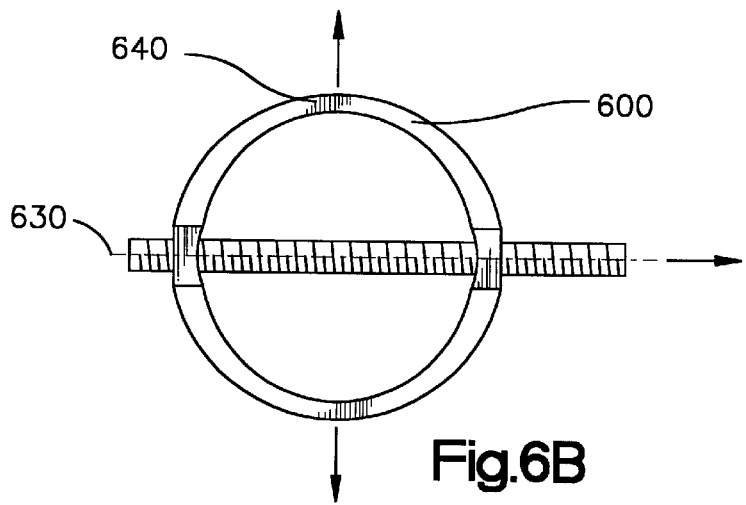
FIG. 6B depicts a cross-sectional perspective of the absorbable block distractor 600 after the distraction screw 630 has been tightened.

Absorbable Block Distractor: This esthetic distractor design, as shown in FIGS. 6A–6B, may consist of a long rectangular block 600 of polylactic acid polymer with a transverse slot 610 and internal threads 620 cut into one of the small ends of the block. As the screw 630 is tightened, the middle portion of the device 640 can be raised, much in the same way that a jack raises a car as its setscrew is tightened (See FIG. 6B). The absorbable block distractor may be placed in the osteotomy and the distraction may be perpendicular to the axis of the screw, permitting intraoral placement of the screw for esthetic distractions. If the device is pulled out without removing the screw first, the bulk of the material could be removed to speed recovery. The screw may be connected at either end to the cable to facilitate this strategy. A variation of this embodiment may comprise the device consisting of a wedge of polylactic acid polymer and a rectangular block, which can be slotted on one side along its minor axis. The distraction screw may transfix the wedge from its base to its apex and drives the wedge into the slot to elevate the leaves of the slot. When the distraction process is finished, the screw may be merely backed out of its hole and the distractor can be left to be absorbed over time. This provides asymmetric distraction for 3-d control with a single device. (See FIGS. 6A–6B)

Figure 7A:
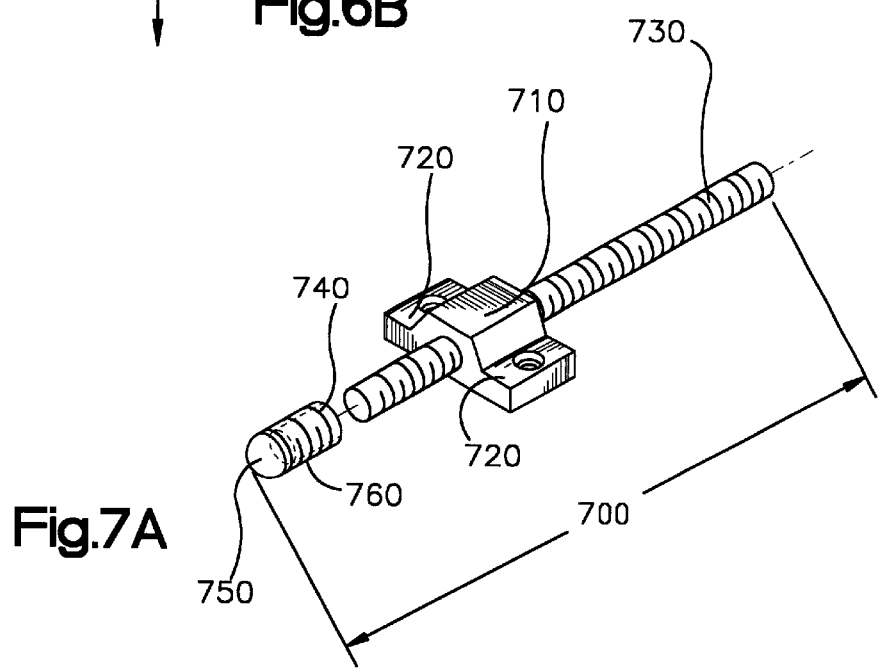
FIG. 7A depicts a schematic of the present invention, specifically showing the midface distractor 700.
Figure 7B:
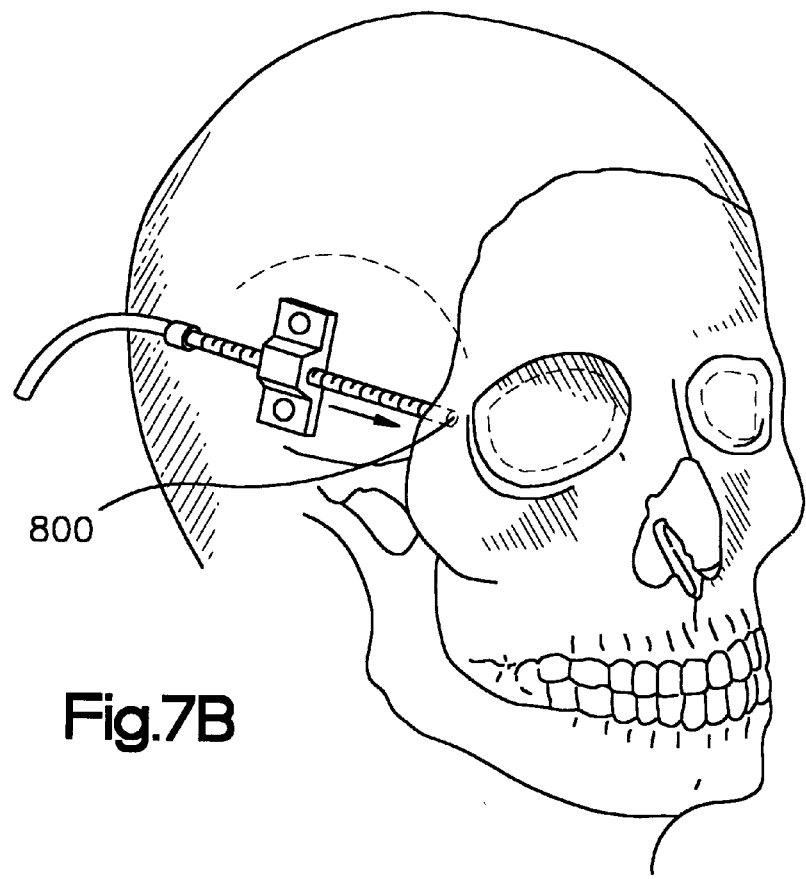
FIG. 7B illustrates the midface distractor 700 affixed to the cranial skeleton.
Figure 7C:
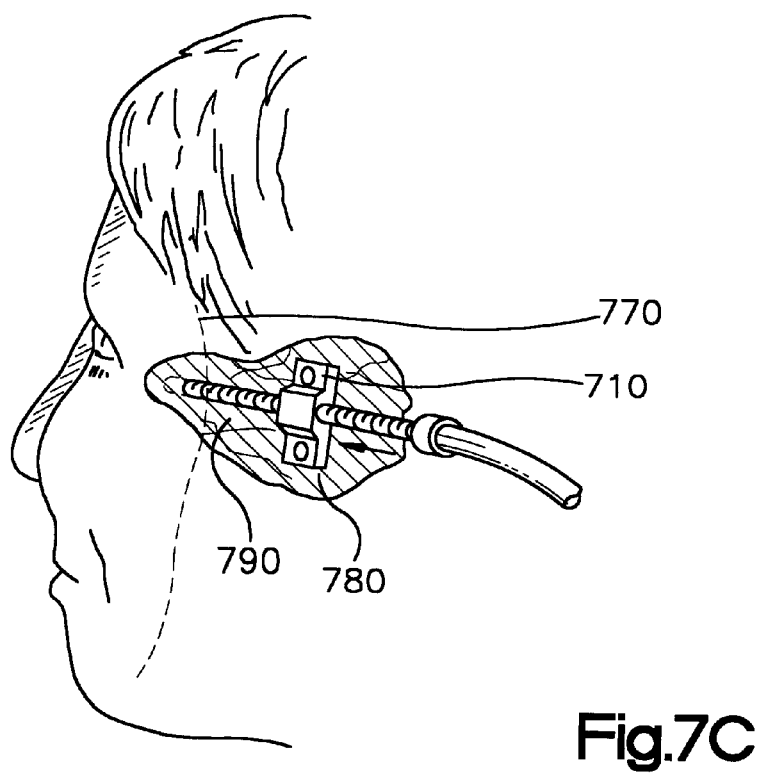
FIG. 7C depicts the base plate of the midface distractor fixed under the muscle 780 in the area of the temporal fossa 790.

Midface distractor: Another example of the present invention comprises a mid-face distractor as shown in FIGS. 7A–7C. The mid-face distractor 700, as shown in FIG. 7A, may consist of a cylindrical block 710 of polylactic acid with footplates 720, which may be affixed to the cranial skeleton in the manner of a plate that would be used in a fracture case, with micro screws. In a further embodiment of the present invention, the micro screws may also be bioabsorbable. In an even further embodiment, if using polymer, a rapid cure polymer may be used to "glue" footplates 720 to the cranial skeleton, which can eliminate the need for micro-screws. The base may be left thicker than the desired final height to be contoured with a burr to coat to the site. In a particular embodiment, this design would be applicable when implanting the midface distractor on the curved floor of the temporal fossa. The distractor screw 730 may pass through the cylinder 710 to provide impetus to the distal portion of the screw (See FIG. 7A). The embodiment may also comprise a distal plug 740, which may consist of a short hollow cylinder with blind-ended 750, external threads 760 (See FIG. 7A).

In the case of a mid-face distraction (See FIGS. 7B–7C), after the facial dysfunction 770 is performed, the base plate 720 is fixed under the muscle 780 in the area of the temporal fossa 790. The distal plug 740 is then inserted into the posterior aspect of the lateral orbital wall 800 in a previously made tunnel. Once the distraction is finished, the screw is merely reversed, and the base plates and the "dummy" cylinder are left to be absorbed. (See FIGS. 7B–7C).

The midface distractor has a variety of corrective applications. It could be used to help correct defects such as the congenital deformity, Crouzon's disease, and also for the treatment of Class III malocclusions as well as for cleft lip and palate.

EXAMPLE THREE

Palatal Distractors

Figure 8A:
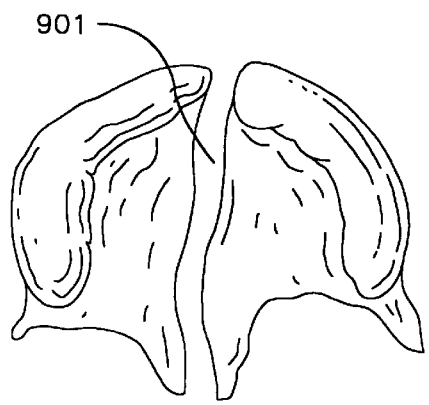
FIG. 8A illustrates a cleft palate.
Figure 8B:
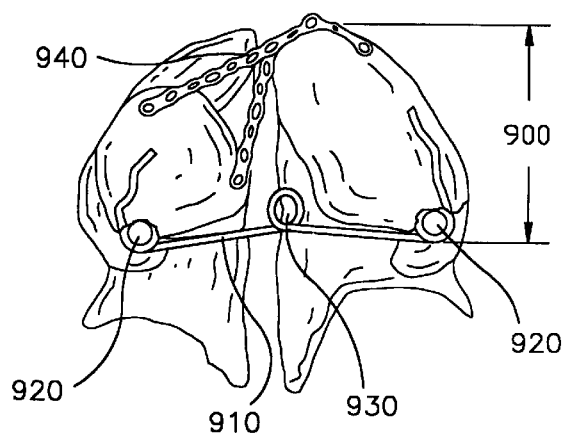
FIG. 8B illustrates an embodiment of the present invention, specifically showing the palatal distractor 900 carrying out the collapse phase.
Figure 8C:
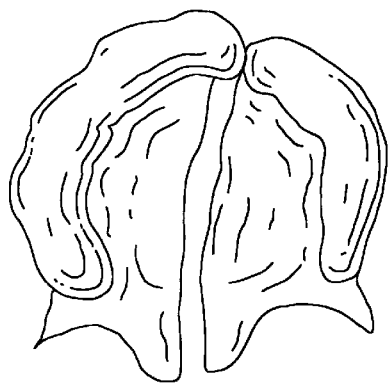
FIG. 8C depicts the cleft palate following the collapse phase and removal of the elastic chain 940.
Figure 8D:
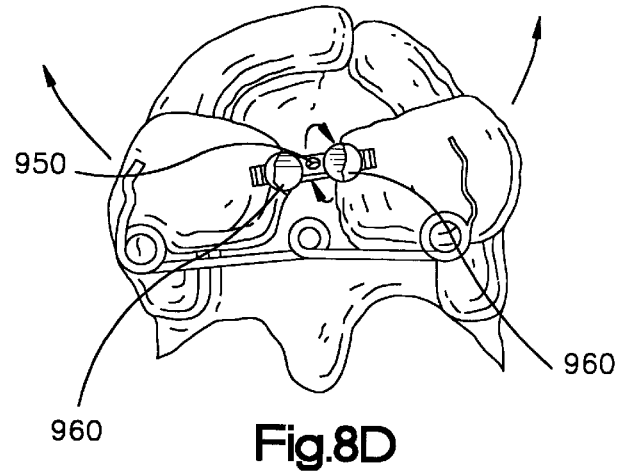
FIG. 8D depicts an embodiment of the present invention, specifically showing the palatal distractor 900 carrying out the expansion phase by widening the palate using a tranverse palatal screw 950.

Palatal Distractor: The present invention may also comprise palatal distractors, which can utilize a splint and can be from materials such as methyl methacrylate or other acrylics to carry out the collapse phase (See FIGS. 8A–8B). The splint 900 may be acrylic with a wire frame 910 with helices at the vertices of the maxillary apophyses 920 and at the midline 930, and can be mounted on the cleft palate 901 with dental adhesive. The buttons may be used to direct elastic chain 940 forces to align the dental segments. A second device, known as a transverse palatal screw 950, may be used to carry out the expansion phase by widening the palate (See FIGS. 8C–8D). This embodiment may be fixed to the palate with permucosal screws 960, which are threaded through the acrylic splint.

In the case of a palate distraction, the palate is collapsed with the acrylic splint until the segments are aligned and in contact. The acrylic is burred down in the area of contact gradually to prevent the apparatus from interfering with the intimate contact. Then, while the patient is under general anesthesia, the primary palate is repaired with an osteoinductive substance such as a rib graft, which is placed in the maxillary defect, then the second device is placed and fixed with screws to the palate, and the lip is repaired. The parents can then activate the screw daily until the correct occlusion is attained. The device is left placed until bony consolidation is demonstrated radiographically.

What is claimed is:

1. An osteogenic distractor for distracting a first bone segment from a second bone segment suitable for indexed osteotomy following permanent implantation into bone, comprising:
   a first member anchored to said first bone segment;
   a second member anchored to said second bone segment;
   a screw for facilitating movement of said first member relative to said second member; and
   a spacer member made of bioabsorbable material configured to accept an indexed osteotomy through axes of said first and second members, said spacer having:
      a first surface initially contiguous with at least one surface of said first member, and
      a second surface initially contiguous with at least one surface of said second member.

2. The distractor of claim 1, wherein said first member and said second member are made of bioabsorbable material.

3. The distractor of claim 1, wherein said bioabsorbable material is selected from one or more of the group consisting of poly-D, L-lactic acid, polyethylene glycol, polydioxanone, polylactic acid, 70L/30DL polylactide, polyglycolide, poly(orthoester), calcium sodium metaphosphate, hydroxyapatite, calcium phosphate, polytetra fluoroethylene, collagen I, II, IX, X, and XI, durapatite, and hydrogel.

4. The distractor of claim 1, further comprising a means for isolating said distractor from an external environment.

5. The distractor of claim 1, wherein said distractor is capable of engaging a dental prosthesis.

6. The distractor of claim 1, further comprising a means for stimulating growth of said bone segments into and around said first member and said second member following implantation.

7. The distractor of claim 1, wherein said screw comprises pre-defined stop points.

8. The distractor of claim 1, further comprising an automated mechanism for controlling said screw.

9. The distractor of claim 1, further comprising a bioabsorbable cap for protecting soft tissue during distraction.

10. The distractor of claim 1, wherein external surfaces of said first and second members are threaded.

11. The distractor of claim 8, wherein a peripheral portion of said spacer member conforms to external threads of said first and second members.

12. The distractor of claim 8, wherein a peripheral portion of said spacer member creates a gap in a thread pattern on external surfaces of said first and second members.

13. The distractor of claim 1, further comprising a healing abutment.

14. The distractor of claim 11, wherein said healing abutment provides a restoration post for accepting a dental restoration.

15. An osteogenic implant and distractor assembly for indexed osteotomy and permanent implantation into bone, the assembly comprising:

first and second axially aligned implant members having external surfaces configured to anchor to bone;

a bioabsorbable spacer member aligned with and between said first and second implant members;

a bioabsobable protective cap aligned with and positioned about a distal end of said second implant member; and an axial screw threaded through a threaded axial bore in said first implant member, an axial bore in said spacer member, a threaded axial bore in said second implant member and into a partial bore in said protective cap;

wherein said spacer member is configured to accept an indexed osteotomy through the axes of said first and second members, said spacer comprising:

a first surface initially contiguous with at least one surface of said first member, and a second surface initially contiguous with at least one surface of said second member.

16. The osteogenic implant and distractor assembly of claim 11, further comprising an O-ring for sealing the assembly within bone matter.

17. A method for the distraction of bone comprising the steps of:

providing a distractor assembly comprising a first member, a second member, a distraction screw in threaded engagement with the first and second members for causing movement of said first member relative to said second member, and a bioabsorbable spacer member having a first surface initially contiguous with a surface of said first member and a second surface initially contiguous with a surface of said second member when the distractor assembly is in an unextended state;

placing said distractor assembly in an unextended state in a predetermined site where bone regeneration is required;

backing said distraction screw out of said distraction device;

performing an osteotomy through said bioabsorbable spacer member to form a distraction gap;

replacing the distraction screw into threaded engagement with the first and second members following the osteotomy; and turning the distraction screw to extend said distractor assembly to widen said distraction gap.

18. The method of claim 15 whereby said osteotomy is performed prior to the integration of said distractor into bone.

19. The method of claim 15 whereby the distraction screw placed into said distraction device following the osteotomy is the same distraction screw that was backed out of said distraction device prior to the osteotomy.

20. The method of claim 15 whereby the distraction screw placed into said distraction device following the osteotomy is a different distraction screw than the screw that was backed out of said distraction device prior to the osteotomy.

21. The method of claim 15 whereby said distraction gap is widened between 0.25 mm and 1.0 mm daily.

22. The method of claim 15 wherein said osteotomy is an indexed osteotomy performed blindly between said first member and said second member.

23. The method of claim 15 further comprising the step of engaging said distraction device to widen said distraction gap.

* * * * *